United States Patent [19]

Fischer et al.

[11] Patent Number: 4,879,404

[45] Date of Patent: Nov. 7, 1989

[54] NOVEL SALICYLATES, THEIR SALTS, PHARMACEUTICAL COMPOSITIONS CONTAINING THEM AND PROCESS FOR PREPARING SAME

[75] Inventors: János Fischer; László Dobay; Mihály Major; Elemér Ezer; Judit Matuz; Katalin Sághy; György Hajós; László Szporny, all of Budapest, Hungary

[73] Assignee: Richter Gedeon Vegyeszeti Gyar Rt, Budapest, Hungary

[21] Appl. No.: 248,970

[22] Filed: Sep. 26, 1988

[30] Foreign Application Priority Data

Sep. 25, 1987 [HU] Hungary .............. 4303/87

[51] Int. Cl.⁴ .............................. C07C 69/76
[52] U.S. Cl. ................................. 560/051
[58] Field of Search .......... 560/51; 514/533

[56] References Cited

U.S. PATENT DOCUMENTS

| | | | |
|---|---|---|---|
| 4,483,868 | 11/1984 | Christidis et al. | 560/51 |
| 4,600,725 | 7/1986 | Garzia | 560/51 |
| 4,689,423 | 8/1987 | Beylin et al. | 560/51 |

FOREIGN PATENT DOCUMENTS

| | | |
|---|---|---|
| 0134179 | 3/1985 | European Pat. Off. |
| 1282644 | 11/1968 | Fed. Rep. of Germany . |
| 1566497 | 4/1980 | United Kingdom . |
| 2075836 | 11/1981 | United Kingdom . |
| 2107714 | 5/1983 | United Kingdom . |

*Primary Examiner*—Paul J. Killos
*Attorney, Agent, or Firm*—Herbert Dubno; Jonathan Myers

[57] ABSTRACT

The present invention relates to novel compounds of the general formula (I),

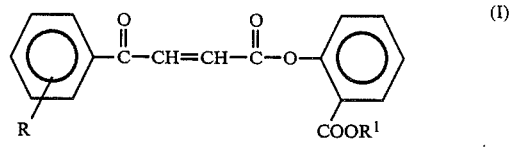

wherein
R stands for hydrogen, halogen, $C_{1-4}$ alkyl, $C_{1-4}$ alkoxy or a $C_{1-4}$ acylamino group; and
$R^1$ is hydrogen or a carboxyl-protective group or E and/or Z configuration as well as their salts.

The compounds according to the invention show a cytoprotecive effect and in addition, a valuable anti-inflammatory action. Their toxicity is low.

11 Claims, No Drawings

NOVEL SALICYLATES, THEIR SALTS, PHARMACEUTICAL COMPOSITIONS CONTAINING THEM AND PROCESS FOR PREPARING SAME

FIELD OF THE INVENTION

This invention relates to novel 4-oxo-4-(substituted phenyl)butenoyl-salicylates of E and/or Z configuration having cytoprotective and in addition, valuable anti-inflammatory action.

BACKGROUND OF THE INVENTION

Several compounds, close to these compounds concerning both their type of activity and chemical structure, have been described in the British patent specification No. 2,096,999. One of the most effective compounds claimed in this cited patent specification was found to be 4-oxo-4-(3,4,5-trimethoxyphpenyl)butenoic acid prepared by dehydratingn acetophenone with glyoxylic acid. The yield of the aldol reaction amounted to 28%, that of the dehydration to 71%, which means a total yield of only 20%.

OBJECT OF THE INVENTION

The object of the present invention is to provide novel, therapeutically useful compounds which can be prepared in a good yield from simple, commercially available starting substances.

SUMMARY OF THE INVENTION

Thus, the present invention relates to novel compounds of the formula (I),

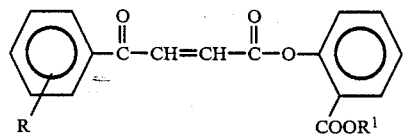

wherein
R stand for hydrogen, halogen, $C_{1-4}$alkyl, $C_{1-4}$alkoxy or a $C_{1-4}$acylamino group; and
$R^1$ is ihydrogen or a carboxyl-protective group of E and/or Z configuration as well as their salts, and pharmaceutical compositions containing these compounds.

The compounds of the formula (I) contain a double bond, and thus can exist in the form of the E or Z geometrical isomer.

According to another aspect of the invention, there is provided a process for the preparation of the new compounds of the formula (I), wherein
R stands for hydrogen, halogen, $C_{1-4}$alkyl, $C_{1-4}$alkoxy or a $C_{1-4}$acylamino group; and
$R^1$ is hydrogen or a carboxyl-protective group of E and/or Z configuration as well as their salts, which comprises
(a) reacting a compound of the formula (II),

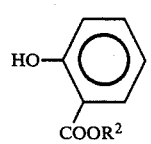

wherein $R^2$ is a carboxyl-protective group, with a substituted butenoic acid of the formula (III),

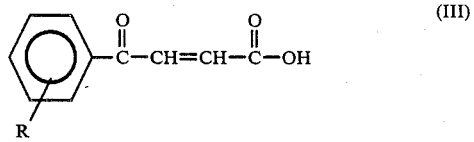

wherein R is as defined above, or with a carboxyl group-activataed derivative thereof and, if desired, removing an optionally present protecive group in a known manner; or
(b) reacting salicylic acid with a compound of the formula (IV),

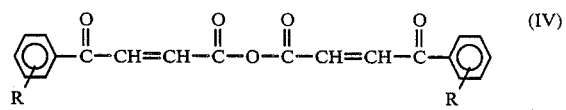

wherein R is as defined above and, if desired, removing an optionally present protective group in a known way from the compound of the formula (I) obtained by using any of the processes (a) or (b) and/or, if desired, changing in the obtained compound of the formula (I) the configuration, determined by the double bond, in a known manner.

If desired, the compounds of the formula (I) containing a free carboxyl group can be converted to pharmaceutically acceptable salts with inorganic or organic bases.

The starting materials are commercially available or can be prepared by methods described in the literature. Thus, the preparation of 4-oxo-4-phenyl-2(E)-butenoic acid has been described in Org. Synth. Coll. Vol. 3, page 109 (1955); 4-(4-methylphenyl)-4-oxo-2(E)-butenoic acid has been prepared according to Pechman [Berichte 15, 888 (1982)] whereas 4-(4-methoxyphenyl)-4-oxo-2(E)-butenoic acid has been synthesized according to Papa et al. [J. Am. Chem. Soc. 70, 3356 (1948)].

It has been found in the course of our investigations that the reaction of the starting substances could be carried out in a yield of 45 to 70% under the usual conditions.

The compounds according to the invention can be prepared in two ways.

According to an embodiment of the process according to the invention, a butenoic acid of the formula (III) is suitably reactedd with a salicylic acid of the formula (II) containing a protected carboxyl group. Useful protective groups are the tert.-butyl, diphenylmethyl, trimethylbenzyl and phthalimidomethyl groups [R. W. Roeske: "The Peptides", Vol. 3., page 101 (1981) as well as T.W. Green: "Protective Groups in Organic Synthesis", Ed. John Wiley, New York, Chichesster, Brisbane, Toronto and Singapore (1981)] may preferably be used for protection. In this process variant a coupling reagent commonly used in peptide chemistry, preferably, N,N-dicyclohexylcarbodiimide is also employed. Other coupling (activating) reagents have been described in a monograph by M. Bodánszky: "Principles of Peptide Synthesis", Springer Verlag, Berlin, Heidelberg, New York and Tokyo (1984). This reactio is carried out in an inert solvent, preferably in anhydrous dichloromethane at a temperature between 0° C. and 20° C.

Alternatively, the compounds according to the invention may also be prepared by reacting a butenoic acid anhydride of the formula (IV) with salicylic acid. This reaction is carried out in an inert organic solvent, preferably in anhydrous dichloromethane or chloroform at a temperature between 20° C. and 80° C. It is advisable to use this process variant only in cases when the target product is easy to separate from the butenoic acid component arising as a side product.

If desired, the E and Z isomers of the compounds of formula (I) can be converted into each other: e.g. a compound of E configuration can be converted to the product of Z configuration under the effect of e.g. UV light in the presence of an inert organic solvent.

The compounds of the formula (I) containing hydrogen as $R^1$ are prepared by removing the group different from hydrogen (suitably the tert.-butyl group), which is bound to the carboxyl group in question, in a known way e.g. by using trifluoroacetic acid.

In the course of our pharmacological study it has been found that, when used even in low doses, the compounds of the formula (I) show a cytoprotective action and, in additio, an antiinflammatory effect is also observed (with an oral $ED_{50}$ value of 2 to 6 mg/kg).

The cytoprotective effect was investigated by using the method of A. Robert [Gastroenterology 77, 761 (1979)] as follows.

Starved rats were given absolute ethanol containing concentrated hydrochloric acid, which induced longitudinal bleeding in the glandular part of the stomach within a short time. This damaging effect is prevented by cyto-protective substances.

The anti-inflammatory action of the compounds according to the invention was investigated by using the carrageenin-induced rat paw edema and the adjuvant polyarthritis test. The anti-inflammatory effect of the compounds examined was about of the same order as that of aspirin.

The oral $ED_{50}$ values of the substances according to the invention proved to be 2 to 6 mg/kg. In addition, the toxicity values were also found to be very favorable since no toxic symptoms were observed after a single oral administration of even 1000 mg/kg.

The invention is illustrated in detail by the following non-limiting Examples.

EXAMPLE 1

Preparation of 2-carboxyphenyl 4-oxo-4-phenyl-2(E)-butenoate

A solution containing 6.6 g (0.047 mol) of salicylic acid and 19.2 g (0.057 mol) of 4-oxo-4-phenyl-2(E)-butenoic acid anhydride in 180 ml of chloroform is stirred at 60° C. under argon for 14 hours. After terminating the reaction, the mixture is cooled to 10° C. and stirred at this temperature for 2 hours. The product is filtered and washed with chloroform to give the named compound in a yield of 10.0 g (71%), m.p.: 154–156° C.

Preparation of the starting substance, 4-oxo-4-phenyl-2(E)-butenoic acid anhydride:

The solution of 30 g (0.170 mol) of 4-oxo-4-phenyl-2(E)-butenoic acid in 150 ml of anhydrous dichloromethane is cooled to 0° C. and a solution containing 17.5 g (0.085 mol) of N,N-dicyclohexylcaarbodiimide in 50 ml of dichloromethane are added at the same temperature. After stirring the reaction mixture at 0° C. for 3 hours, the precipitated dicyclohexylurea is filtered and after evaporating the solvent under vacuo, the oily residue is crystallized from methanol to give 19.4 g (70%) of 4-oxo-4-phenyl-2(E)-butenoic acid anhydride, m.p.: 114-116° C.

EXAMPLE 2

Preparation of 2-carboxyphenyl 4-(4-chlorophenyl)-4-oxo-2(E)-butenoate

The solution of 6.32 g (0.03 mol) of 4-(4-chlorophenyl)-4-oxo-2(E)-butenoic acid and 5.82 g (0.03 mol) tert.-butyl salicylate in 100 ml of anhydrous dichloromethane is cooled to 0° C., then 6.19 g (0.03 mol) of N,N-dicyclohexylcaarbodiimide dissolved in 20 ml of anhydrous dichloromethane are added. After stirring the reaction mixture at 0° C. for 2 hours, the precipitated dicyclohexylurea is filtered and the filtrate is successively extracted with 1N hydrochloric acid, water, saturated aqueous sodium carbonate solution and finally with saturated sodium chloride solution. After drying over anhydrous magnesium sulfate and evaporating the solvent, the oily residue is dissolved in 10 ml of dichloromethane, cooled to 0° C. and a mixture containing 20 ml of trifluoroacetic acid and 20 ml of anhydrous dichloromethane is added. After keeping the solution at 0° C. for 15 minutes, it is allowed to warm to room temperature. After standing for 1 hour, the mixture is evaporated and the oily residue is crystallized from ethyl acetate to give 4.76 g (48%) of the named compound, m.p. 164°–166° C.

EXAMPLE 3

Preparation of 2-carboxyphenyl 4-(4-methylphenyl)-4-oxo-2(E)-butenoate

The solution of 3.80 g (0.02 mol) of 4-(4-methylphenyl)-4-oxo-2(E)-butenoic acid and 3.88 g (0.02 mol) of tert.-butyl salicylate in 80 ml of anhydrous dichloromethane is cooled to 0° C. and 4.12 g (0.02 mol) of N-N-dicyclohexylcarbodiimide dissolved in 20 ml of anhydrous dichloromethane are added at the same temperature. After stirring the reaction mixture at O ° C. for 2 hours, the precipitated dicyclohexylurea is filtered and the filtrate is successively extracted with 1N hydrochloric acid, water, saturated aqueous sodium carbonate solution and finally with saturated sodium chloride solution. After drying over anhydrous magnesium sulfate and evaporating the solvent, the oily residue is dissolved in 20 ml of anhydrous dichloromethane, cooled to 0° C. and 40 ml of an 1:1 mixture of trifluoroacetic acid with dichloromethane are added. After keeping the solution at 0° C. for 15 minutes, the temperature of the solution is allowed to get to room temperature and after standing for 1 hour, the solvent is evaporated under vacuo to give 2.80 g(45%) of the named compound, m.p.: 114°–116° C.

EXAMPLE 4

Preparation of 2-carboxyphenyl 4-(4-methoxyphenyl)-4-oxo-2(E)-butenoate

The solution of 8.3 (0.04 mol) of 4-(4-methoxyphenyl)-4-oxo-2(E)-butenoic acid and 7.85 g (0.04 mol) of tert.-butyl salicylate in 120 ml of anhydrous dichloromethane is cooled to 0° C., then 8.3 g (0.04 mol) of N-N-dicyclohexylcarabodiimide dissolved in 25 ml of anhydrous dichloromethane are added. After stirring the reaction mixture at 0° C. for 2 hours, the precipitated dicyclohexylurea is filtered and the filtrate is successively extracted with 1N hydrochloric acid, waater, saturated sodium carbonate solution and finally with saturated sodium chloride solution. After drying over anhydrous magnesium sulfate and evaporating the solvent, the oily residue is dissolved at 0° C. in a mixture of 25 ml of tribluoroacetic acid and 25 ml of anhydrous dichloromethane. The solution is slowly allowed to warm to room temperature and after evaporating the solvent under vacuo the residue is crystallized from ethyl acetate to give 6.7 g (52%) of the named compound, m.p.: 150°–152° C.

EXAMPLE 5

Preparation of 2-carboxyphenyl 4-oxo-4-phenyl-2(E)-butenoate

After cooling to 0° C. a solution containing 8.1 g (0.046 mol) of 4-oxo-4-phenyl-2(E)-butenoic acid and 9.0 g (0.046 mol) of tert.-butyl salicylate in 60 ml of anhydrous dichloromethane, 9.5 g (0.046 mol) of N,N-dicyclohexylcarbodiimide dissolved in 20 ml of anhydrous dichloromethane are added at the same temperature. After stirring the reaction mixture at 0° C. for 20 hours, the precipitated dicyclohexylurea is filtered and the filtrate is successively extracted with 1N hydrochloric acid, water, 5% sodium carbonate solution and finally with saturated sodium chloride solution. After drying the solution over anhydrous magnesium sulfate and evaporating the solvent, the oily residue is dissolved in 120 ml of an 1:1 mixture of anhydrous dichloromethane and trifluoroacetic acid under cooling by water and the solution is let to stand at room temperature for 1 hour. After evaportion of the solvent, the residue is crystallized from ethyl acetate to give 7.5 g (55%) of the title compound, m.p.: 154°–156° C.

We claim:

1. A 4-Oxo-4-(substituted phenyl)butenoyl-salicylate of the formula (I),

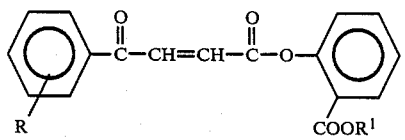

wherein

R stands for hydrogen, halogen, $C_{1-4}$alkyl, $C_{1-4}$alkoxy or a $C_{1-4}$acylamino group;; and $A^1$ is hydrogen or a carboxyl-protective group of E and/or Z configuratio or a salt thereof.

2. 2-Carboxyphenyl 4-oxo-4-phenyl-2(E)-butenoate as defined in claim 1.

3. 2-Carboxyphenyl 4-(4-methoxyphenyl)-4-oxo-2(E)-butenoate as defined in claim 1.

4. A pharmaceutical composition, which comprises as active ingredient a 4-oxo-4-(substituted phenyl)butenoyl-salicylate of the formula (I),

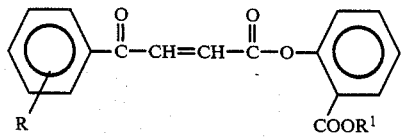

wherein

R stands for hydrogen, halogen, $C_{1-4}$alkyl, $C_{1-4}$alkoxy or a $C_{1-4}$acylamino group; and $R_1$ is hydrogen or a carboxyl-protective group of E and/or Z configuration or a pharmaceutically acceptable salt thereof, in admixture with a pharmaceutical carrier.

5. A pharmaceutical composition as defined in claim 4, which comprises as active ingredient 2-carboxyphenyl 4-oxo-4-phenyl-2(E)-butenoate or a pharmaceutically acceptable saltl thereof, in admixture with a pharmaceutical carrier.

6. A pharmaecutical composition as defined in claim 4, which comprises as active ingredient 2-carboxyphenyl 4-(40methoxyphenyl)-4-oxo-2(E)-butenoate or a pharmaceutically acceptable salt thereof, in admixture with a pharmaceutical carrier.

7. A process for the preparation of 4-oxo-4-(substituted phenyl)butenoyl-salicylates of othe formula (I),

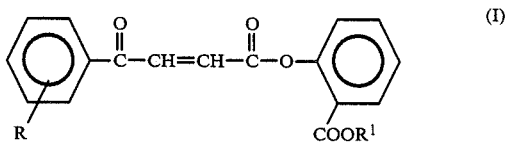

wherein

R stands for hydrogen, halogen, $C_{1-4}$alkyl, $C_{1-4}$alkoxy or a $C_{1-4}$acylamino group; and $R^1$ is hydrogen or a carboxyl-protective group of E and/or Z configuration or a salt thereof, which comprises (a) reacting a compound of the formula (II),

wherein $R^2$ is a carboxyl-protective group, with a substituted butenoic acid of the formula (III)

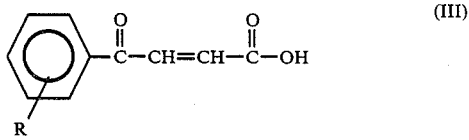

or with a carboxyl group-activated derivative thereof and optionally removing an optionally present protective group; or (b) reacting salicylic acid with a compound of the formula (IV),

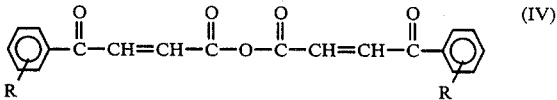

and, optionally removing an optionally present protective group from the compound of the formula (I) obtained by using any of steps (a) or (b) and optionally changing in the obtained compound of the formula (I) the configuration, determined by the double bond.

8. A process as claimed in claim 7, which comprises using a substituted butenoic acid of the formula (III) activated by a carbodiimide.

9. A process as claimed in claim 7, which comprises changing the configuration, determined by the double bond, in the compounds of the formula (I), by using UV light.

10. A process as defined in claim 7 for the preparation of a pharmaceutical composition, which comprises mixing as active ingredient a 4-oxo-4-(substituted phenyl)-butenoyl-salicylate of the formula (I), wherein
 R stands for hydrogen, halogen, $C_{1-4}$alkyl, $C_{1-4}$alkoxy or a $C_{1-4}$acylamino group; and
 $R^1$ is hydrogen or a carboxyl-protective group of E and/or Z configuration or a pharmaceutically acceptable salt thereof with a pharmaceutical carrier.

11. A cytoprotective and anti-inflammatory method of treatment which comprises administering an effective amount of a compound as defined in claim 1 to a mammalian subject having an inflammatory indication.

* * * * *